(12) United States Patent
Hsu et al.

(10) Patent No.: US 8,876,744 B2
(45) Date of Patent: Nov. 4, 2014

(54) SYSTEMS AND METHODS FOR CONTROLLING CEREBROSPINAL FLUID IN A SUBJECT'S VENTRICULAR SYSTEM

(75) Inventors: David Ambrose Hsu, Middleton, WI (US); Bermans J Iskandar, Madison, WI (US); Murielle Aline Hsu, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 174 days.

(21) Appl. No.: 13/040,942

(22) Filed: Mar. 4, 2011

(65) Prior Publication Data
US 2012/0226215 A1 Sep. 6, 2012

(51) Int. Cl.
*A61M 5/00* (2006.01)
*A61M 27/00* (2006.01)

(52) U.S. Cl.
CPC ..... *A61M 27/006* (2013.01); *A61M 2202/0464* (2013.01)
USPC ................................. 604/9; 604/10

(58) Field of Classification Search
USPC ................................... 604/8, 9, 10
See application file for complete search history.

(56) References Cited

U.S. PATENT DOCUMENTS

| 5,156,600 A * | 10/1992 | Young ........................... 604/247 |
| 6,689,085 B1 * | 2/2004 | Rubenstein et al. .............. 604/9 |
| 7,025,739 B2 * | 4/2006 | Saul ................................. 604/9 |
| 2005/0038371 A1 * | 2/2005 | Reich et al. ...................... 604/9 |

OTHER PUBLICATIONS

Egnor et al; A model of intracranial Pulsations; Pediatr Neurosurg 2001; 35:284-298 Oct. 2001.
Bergsneider et al; What we don't (but should) know about hydrocephalus; JNeurosurg (3 Suppl Pediatrics) vol. 104, 157-159; Mar. 2006.
Wagshul et al; Resonant and notch behavior in intracranial pressure dynamics; JNeurosurgPediatrics3: 354-364, May 2009.
Zou et al; Intracranial pressure waves: characterization of a pulsation absorber with notch filter properties using systems analysis; JNeurosurg Pediatrics vol. 2, 83-94; Jul. 2008.

* cited by examiner

*Primary Examiner* — Tatyana Zalukaeva
*Assistant Examiner* — Benjamin Klein
(74) *Attorney, Agent, or Firm* — Quarles & Brady, LLP (57) ABSTRACT

A system for draining excess cerebrospinal fluid (CSF) from the head of a subject includes a drainage shunt and a valve assembly that selectively permits the shunt to drain CSF. The valve assembly also compensates for multiple factors that can affect the subject's intracranial pressure (ICP) and compliance, and could otherwise lead to CSF over-drainage or other undesirable conditions.

22 Claims, 5 Drawing Sheets

SYSTEMS AND METHODS FOR CONTROLLING CEREBROSPINAL FLUID IN A SUBJECT'S VENTRICULAR SYSTEM

CROSS-REFERENCE TO RELATED APPLICATION

Not applicable.

STATEMENT OF FEDERALLY SPONSORED RESEARCH OR DEVELOPMENT

Not applicable.

BACKGROUND OF THE DISCLOSURE

The present disclosure generally relates to systems and methods for controlling cerebrospinal fluid in a subject's ventricular system and, more particularly, to systems and methods that control the cerebrospinal fluid such that the average intracranial pressure is maintained within a specific range.

Hydrocephalus is a disorder in which a subject's body produces cerebrospinal fluid (CSF) at a rate faster than the venous system absorbs the fluid. The increased intracranial pressure (ICP) caused by the excess fluid can lead to a number of uncomfortable and potentially dangerous neurological symptoms, such as headaches, cerebral edema, and intracranial hematoma.

Traditional treatment for hydrocephalus involves connecting a drainage shunt between a subject's ventricular system, in which CSF accumulates, and another body cavity, such as the peritoneal cavity. As such, CSF drains from the subject's ventricular system and is absorbed by tissue proximate the shunt outlet.

In some cases, unfortunately, drainage shunts can lead to slit ventricle syndrome. With this disorder, the shunt over-drains the CSF in the ventricular system. The reduced amount of CSF in the ventricular system results in low ICP, which in turn causes ventricular ependymal tissue to collapse around the shunt inlet. The low ICP can result in debilitating headache and, in more severe cases, dural hemorrhage. The collapse of ventricular ependymal tissue around the shunt inlet can also block entry of CSF into the shunt system. Over time, such shunt obstruction can lead to a rise in ICP. With repeated cycles of low and high ICP, complete blockage of the shunt inlet can occur, leading to potentially life-threatening shunt failure. In this case, the shunt must be urgently replaced.

In an attempt to address slit ventricle syndrome and CSF over-drainage, some shunts include a valve that inhibits continuous CSF drainage and attempts to maintain generally constant ICP. In particular, such valves typically prevent CSF drainage from the ventricular system unless a pressure differential threshold across the valve is exceeded. Unfortunately, some subjects using these shunt/valve systems nevertheless develop slit ventricle syndrome, for reasons that are, generally, unclear.

Research has lead some to deduce that, in some cases, subjects develop slit ventricle syndrome even when using the above shunt/valve systems due to the varying effect of gravity on CSF pressure as the subject changes orientation (e.g., as the subject moves from a supine to an upright orientation or vice versa). In contrast to when a subject lies in a supine orientation, the weight of the CSF in the ventricular system and in the shunt itself can act on the valve when the patient is upright. This load on the valve leads to inappropriate actuation, once again causing CSF over-drainage and decreased ICP. In some shunt/valve systems, the valve is repositioned and the path of the shunt passageway is modified to reduce the amount of CSF weight that the valve resists. In these cases, however, the valve is still subjected to inappropriate actuation due to siphon effects, which arise due to the weight of CSF in the shunt tubing itself.

Some shunt systems include structures that compensate for such gravitational pressure effects, but even in these cases, some subjects nevertheless experience CSF over-drainage and develop slit ventricle syndrome. Moreover, drainage shunts that incorporate a series of valves or structures for compensating for gravitational pressure effects, empirically, seem to be able to delay, but not prevent, the development of slit ventricle syndrome. When gravitational effects are compensated for, research has yet to definitively explain occurrences of slit ventricle syndrome.

Considering the drawbacks of previous hydrocephalus treatment stents, what is needed in the art is a system for controlling cerebrospinal fluid in a subject's ventricular system in a manner that inhibits CSF over-drainage.

SUMMARY OF THE INVENTION

In one aspect, the present invention provides a system for draining excess CSF from the head of a subject having hydrocephalus. The system includes a drainage shunt and a valve assembly that selectively permits the shunt to drain CSF from the subject's head. In addition, the valve assembly compensates for multiple factors that can affect the subject's ICP and could otherwise lead to CSF over-drainage.

In one aspect, the present invention provides a system for controlling cerebrospinal fluid in a ventricular system of a subject. The system includes a shunt that has a drainage inlet configured to be disposed in the ventricular system of the subject to receive the cerebrospinal fluid. A drainage passageway is in fluid communication with the drainage inlet to receive the cerebrospinal fluid, and a drainage outlet is in fluid communication with the drainage passageway to receive the cerebrospinal fluid. The drainage outlet is configured to be disposed in a region of the subject spaced apart from the ventricular system to drain the cerebrospinal fluid from the ventricular system. The system further includes a cardiac pulse compensation unit connected to the shunt. The cardiac pulse compensation unit includes a drainage valve configured to permit the cerebrospinal fluid to flow toward the drainage outlet when an input pressure of the cerebrospinal fluid at the drainage valve exceeds a first pressure threshold. The cardiac pulse compensation unit further includes a return valve configured to permit the cerebrospinal fluid to return to the ventricular system when the input pressure falls below a second pressure threshold. The system further includes a gravitational force compensation unit connected to the shunt. The gravitational force compensation unit is configured to permit the cerebrospinal fluid to flow toward the drainage outlet when an input pressure of the cerebrospinal fluid at the gravitational force compensation unit exceeds a third pressure threshold. The gravitational force compensation unit varies the third pressure threshold such that a gravitational contribution to an intracranial pressure remains generally constant regardless of subject orientation.

In another aspect, the present invention provides a system for controlling cerebrospinal fluid in a ventricular system of a subject. The system includes a shunt that has a drainage inlet configured to be disposed in the ventricular system of the subject to receive the cerebrospinal fluid. A drainage passageway is in fluid communication with the drainage inlet to receive the cerebrospinal fluid, and a drainage outlet is in fluid communication with the drainage passageway to receive the cerebrospinal fluid. The drainage outlet is configured to be disposed in a region of the subject spaced apart from the ventricular system to drain the cerebrospinal fluid from the ventricular system. The system further includes a valve assembly connected to the shunt. The valve assembly is configured to permit the cerebrospinal fluid to flow from the drainage inlet, through the drainage passageway, and toward the drainage outlet. In addition, the valve assembly is configured to maintain an average intracranial pressure inclusively between a first pressure threshold and a second pressure threshold regardless of cardiac pulse effects and subject orientation.

In yet another aspect, the present invention provides a system for controlling cerebrospinal fluid in a ventricular system of a subject. The system includes a shunt that has a drainage inlet configured to be disposed in the ventricular system of the subject to receive the cerebrospinal fluid. The shunt further includes a drainage outlet in fluid communication with the drainage inlet to receive the cerebrospinal fluid. The drainage outlet is configured to be disposed in a region of the subject spaced apart from the ventricular system to drain the cerebrospinal fluid from the ventricular system. The system further includes a valve assembly connected to the shunt. The valve assembly is configured to permit the cerebrospinal fluid to flow from the drainage inlet and into the valve assembly when an input pressure of the cerebrospinal fluid exceeds a first pressure threshold. The valve assembly is also configured to permit the cerebrospinal fluid to flow from the valve assembly and return to the ventricular system when the input pressure falls below a second pressure threshold. In addition, the valve assembly is configured to permit the cerebrospinal fluid to flow from the valve assembly to the drainage outlet when an intermediate pressure of the cerebrospinal fluid within the valve assembly exceeds a third pressure threshold. The valve assembly varies the third pressure threshold such that a gravitational contribution to an intracranial pressure remains generally constant regardless of subject orientation.

In yet another aspect, the present invention provides a system for controlling cerebrospinal fluid in a ventricular system of a subject. The system includes a shunt that has a drainage inlet configured to be disposed in the ventricular system of the subject to receive the cerebrospinal fluid. A drainage passageway is in fluid communication with the drainage inlet to receive the cerebrospinal fluid. A drainage outlet is in fluid communication with the drainage passageway to receive the cerebrospinal fluid. The drainage outlet is configured to be disposed in a region of the subject spaced apart from the ventricular system to drain the cerebrospinal fluid from the ventricular system. The system further includes a cardiac pulse compensation unit connected to the shunt. The cardiac pulse compensation unit is configured to permit the cerebrospinal fluid to flow from the drainage inlet toward the drainage outlet when an input pressure of the cerebrospinal fluid exceeds a first pressure threshold. The cardiac pulse compensation unit is further configured to permit the cerebrospinal fluid to return to the ventricular system when the input pressure falls below a second pressure threshold. The system further includes a gravitational force compensation unit connected to the shunt. The gravitational force compensation unit is configured to permit the cerebrospinal fluid to flow from the drainage passageway to the drainage outlet when an input pressure of the cerebrospinal fluid at the gravitational force compensation unit exceeds a third pressure threshold. The gravitational force compensation unit varies the third pressure threshold such that a gravitational contribution to an intracranial pressure remains generally constant regardless of subject orientation.

The foregoing and other objects and advantages of the invention will appear in the detailed description that follows. In the description, reference is made to the accompanying drawings that illustrate a preferred configuration of the invention.

DETAILED DESCRIPTION OF THE INVENTION

Figure 1:
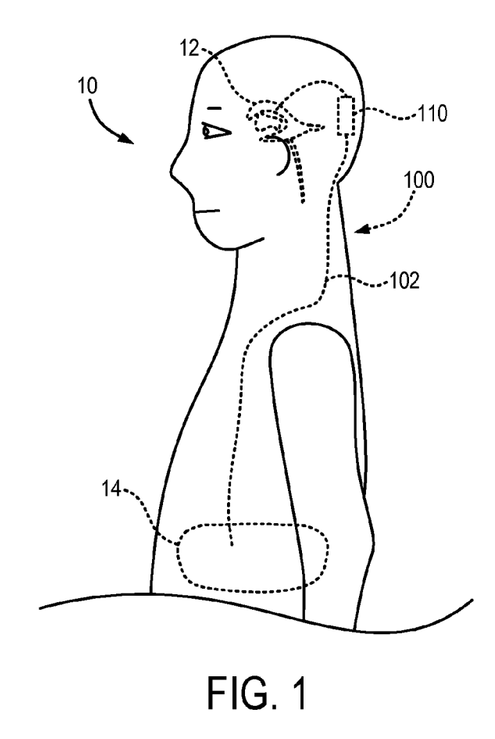
FIG. 1 is a schematic view of a system for controlling cerebrospinal fluid according to the present invention.
Figure 2:
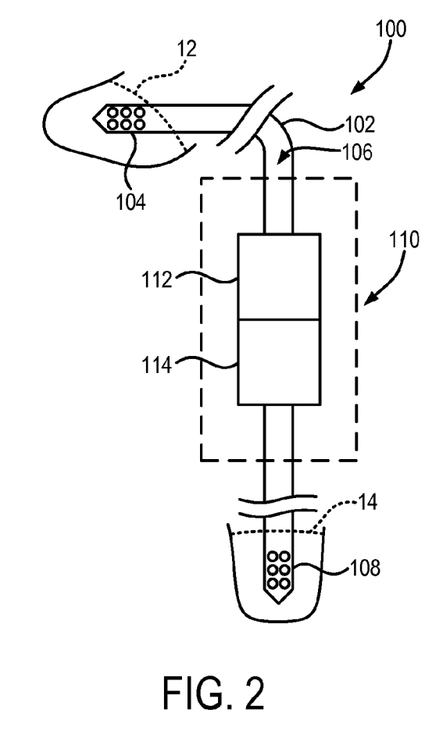
FIG. 2 is a schematic view of the system of FIG. 1 illustrating a valve assembly.

Referring first to FIGS. 1 and 2, the present invention provides a system 100 for draining excess CSF from the head of a subject 10; for example, the subject 10 may be diagnosed as having hydrocephalus. In general, the system includes a shunt 102 that has an inlet 104 disposed in the ventricular system 12 of the subject 10. The inlet 104 is in fluid communication with a shunt passageway 106 that directs CSF toward an outlet 108 disposed in a body cavity capable of absorbing CSF, such as the peritoneal cavity 14. The system 100 also includes a valve assembly 110 that is actuatable to selectively permit CSF flow from the ventricular system 12 toward the peritoneal cavity 14. As described in further detail in the following paragraphs, the valve assembly 110 compensates for multiple factors that can affect the subject's ICP and could otherwise lead to CSF over-drainage or other undesirable conditions. The system 100 compensates for these factors in a manner that inhibits the average ICP from deviating from a predetermined range. In particular, the system 100 drains excess CSF and relieves the increased ICP associated with hydrocephalus and controls CSF over-drainage and the decreased ICP that can lead to development of slit ventricle syndrome. It also allows for control of the compliance of the ventricular system.

As briefly noted in the previous paragraph, the inventors of the present invention have recognized that multiple factors affect a subject's ICP and can lead to CSF over-drainage and to abnormal compliance. In particular, the inventors discovered that, with the previous shunt/valve systems, CSF over-drainage could occur due to both gravitational effects and the relatively-high peak pressures caused by cardiac pulses. In the case of the latter, a conventional pressure-control valve would be actuated even though the average pressure of the CSF was not high enough to facilitate actuation. As such, small amounts of CSF would be unintentionally drained from the ventricular system with each cardiac pulse. Over time, this process can compound and be exacerbated to undesired drainage conditions.

As will be described, the system 100 according to the present invention has a multi-faceted control system and process configured to address the varied and, from some perspectives, independent and distinct, factors that can lead to undesired CSF levels. Referring now to FIG. 2, the control system or valve assembly 110 includes a first, cardiac pulse compensation, unit 112 and a second, gravitational force compensation, unit 114. Turning first to the former unit, the cardiac pulse compensation unit 112, as the name implies, inhibits CSF over-drainage to the peritoneal cavity 14 due to cardiac pulsation. To this end and in some configurations, the cardiac pulse compensation unit 112 is configured to monitor CSF pressure at an inlet of an internally housed control, such as valves that will be described in detail hereafter. When the inlet pressure exceeds a certain threshold due to excess CSF production, the cardiac pulse compensation unit 112 actuates the control. This action permits CSF flow from the ventricular system 12 and into the valve assembly 110. Also, as will be described, if the inlet pressure falls below a certain pressure threshold due to CSF over-drainage, CSF is permitted to flow from the valve assembly 110 and return to the ventricular system 12. It is contemplated that the above functionality may be achieved using mechanical mechanisms, such as valve systems, using electrical/electronic mechanisms, such as sensors, controllers, microprocessors, and electronic valve systems, or using combinations of mechanical and electrical/electronic mechanisms.

The gravitational force compensation unit 114, as the name implies, compensates for gravitational effects on CSF pressure that could otherwise cause over-drainage. In particular, the gravitational force compensation unit 114 reduces the actuating pressure of an internally housed control when the subject 10 is in a supine orientation (i.e., laying down). In such instances when the subject 10 is in the supine orientation, the gravitational force compensation unit 114 need not resist the weight or siphoning effects of CSF. In contrast, when the subject 10 is in an upright orientation, the gravitational force compensation unit 114 is configured to increase the actuating pressure to resist the weight or siphoning effects of CSF in the shunt passageway 106. As will be described, like the cardiac pulse compensation unit 112, it is contemplated that the above functionality may be achieved using mechanical mechanisms, such as valve systems, using electrical/electronic mechanisms, such as sensors, controllers, microprocessors, electronic valve systems, and the like, or using combinations of mechanical and electrical/electronic mechanisms.

Figure 3:
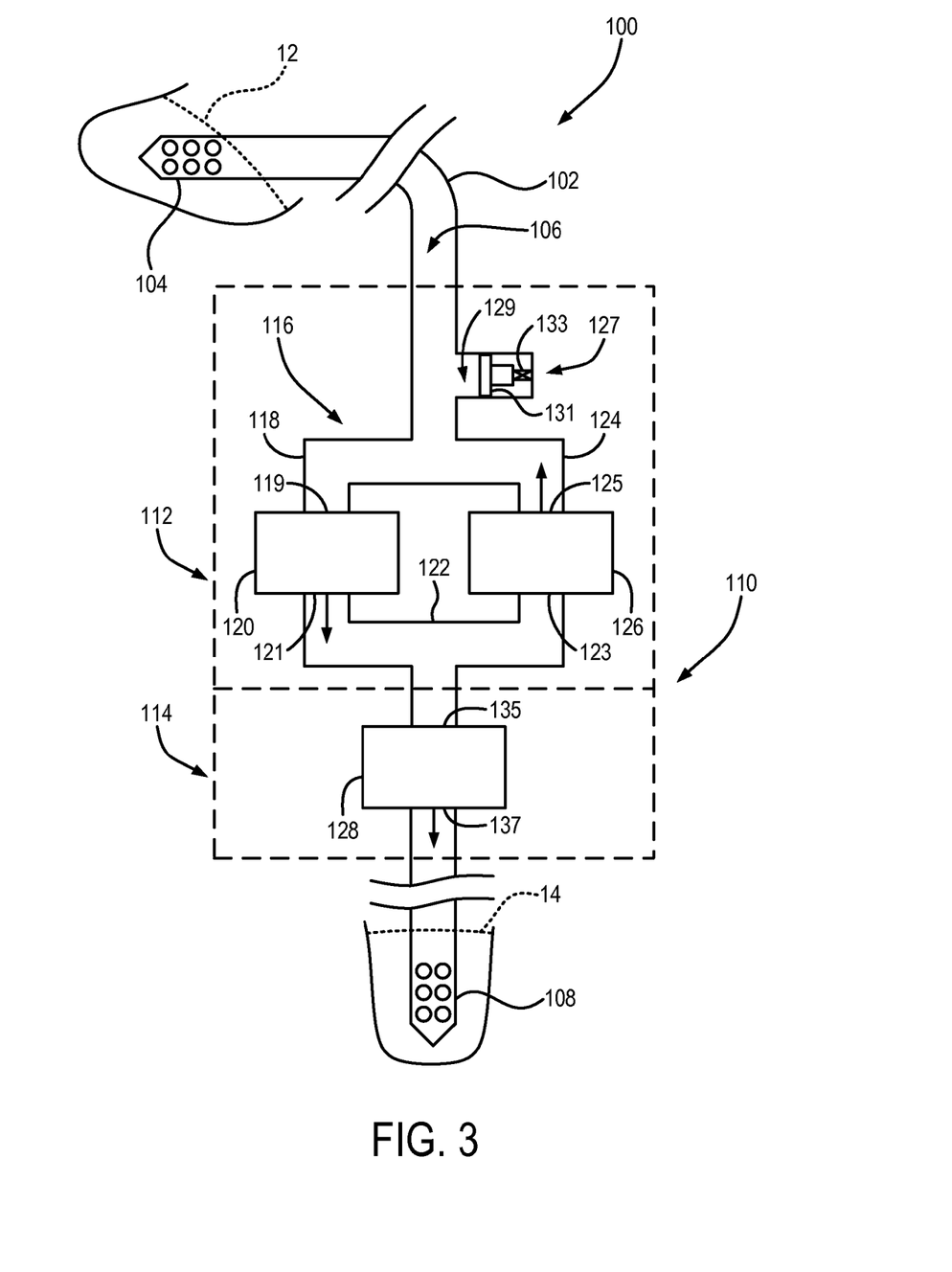
FIG. 3 is a schematic view of an configuration of the valve assembly of FIG. 2 including a cardiac pulse compensation unit and a gravitational force compensation unit.
Figure 4:
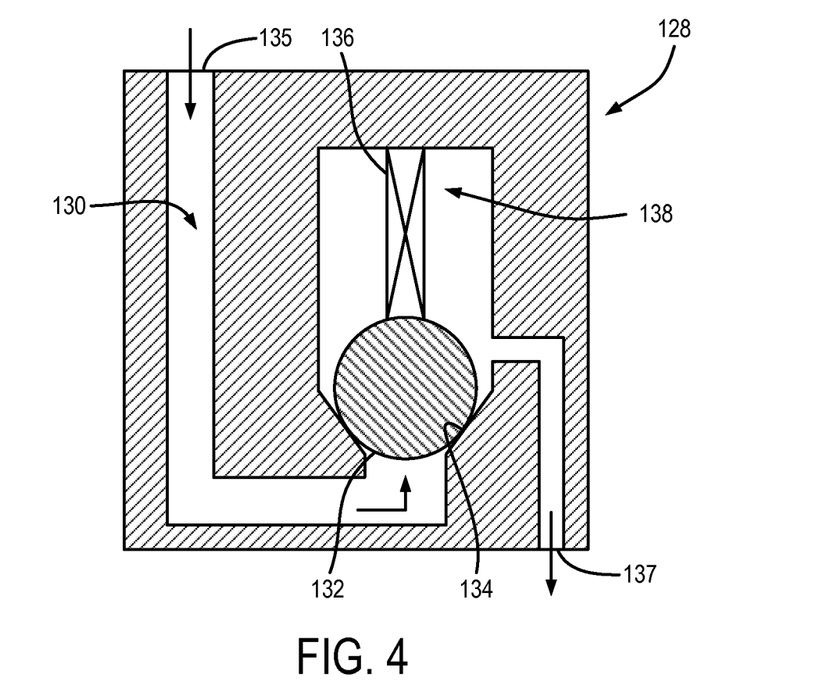
FIG. 4 is a cross-sectional view of the gravity compensation valve FIG. 3.

Referring now to FIGS. 3 and 4, in some configurations the valve assembly 110 may be constructed without electronic sensors and controllers. Specifically, in these configurations the cardiac pulse compensation unit 112 includes a return loop/valve structure 116 that inhibits CSF over-drainage due to the subject's pulse. To this end, the loop/valve structure 116 may include two separate branches that each include a valve.

An inlet branch 118 of the loop/valve structure 116 includes a drainage valve 120 that is preferably a one-way pressure-differential valve. That is, the drainage valve 120 actuates when the pressure difference between the valve's inlet 119 and outlet 121 exceeds a certain pressure differential threshold, $\Delta_d$. As such, the drainage valve 120 is actuatable to permit CSF flow from the ventricular system 12 toward the peritoneal cavity 14.

When operating at steady-state conditions, the inlet branch 118 and the drainage valve 120 facilitate CSF flow as follows. CSF over-production causes excess CSF to accumulate within the subject's ventricular system 12 and within the shunt passageway 106 between the shunt inlet 104 and the drainage valve inlet 119. This in turn causes CSF pressure in the ventricular system 12, or the subject's ICP, and CSF pressure approaching the drainage valve inlet 119 to increase. The pressure continues to increase until the drainage pressure differential threshold $\Delta_d$ is exceeded. The drainage valve 120 then actuates to permit CSF flow into the intermediate shunt passageway 122 at an drainage flow rate, $b_d$, until the drainage pressure differential threshold $\Delta_d$ is no longer exceeded. Such an action reduces the ICP, and the above steps then repeat.

As described briefly above, the subject's pulse can also cause the ICP and the CSF pressure at the drainage valve inlet 119 to increase momentarily. If the drainage pressure differential threshold $\Delta_d$ is exceeded due to this pressure increase, the drainage valve 120 opens momentarily to permit a small amount of CSF flow into the intermediate passageway 122. However, this CSF drainage to the intermediate passageway 122 is considered inappropriate because it occurred due to cardiac pulse effects instead of CSF over-production. This drainage also causes the mean ICP to decrease, and it can cause the mean ICP to decrease to values that cause undesirable symptoms.

In order to compensate for CSF over-drainage to the intermediate passageway 122 as described above, the loop/valve structure 116 also includes a return branch 124 that has a return valve 126. Like the drainage valve 120, the return valve 126 is preferably a one-way pressure-differential valve that actuates when the pressure difference between the valve's inlet 123 and outlet 125 exceeds a certain pressure differential threshold, $L_r$. However, the 123 inlet and outlet 125 of the return valve 126 are oriented to face in a direction opposite to that of the inlet 119 and outlet 121, respectively, of the drainage valve 120. As such, the return valve 126 is actuatable in the opposite direction relative to the drainage valve 120 to permit CSF to flow from the intermediate passageway 122 back toward the ventricular system 12 in the case of over-drainage.

When operating at steady state conditions, the return valve 126 facilitates CSF flow as follows. The drainage valve 120 actuates to permit CSF flow into the intermediate passageway 122 as described above. However, the return pressure differential threshold $\Delta_r$ may be exceeded if cardiac pulse effects cause CSF over-drainage to the intermediate passageway 122 and the ICP correspondingly decreases. In this case, the return valve 126 actuates to permit CSF flow from the intermediate passageway 122 back toward the ventricular system 12 until the return pressure differential threshold $\Delta_r$ is no longer exceeded.

Moreover, the return valve 126 preferably permits CSF flow therethrough at a return flow rate, $b_r$, that is greater than the drainage flow rate, $b_d$, through the drainage valve 120. This permits the return valve 126 to return CSF to the ventricular system 12 at least as quickly as the drainage valve 120 drains CSF from the ventricular system 12.

In some situations, the subject's instantaneous ICP can be higher than that permitted by the forward and return valve system 112 and 126 because of a response lag in the return loop/valve structure 126 to sudden pressure changes. As such, the ICP can have relatively high peak pressures due to cardiac pulses. These high peak pressures can cause symptoms such as headache. To dampen these peak pressures and other sudden pressure changes, in some configurations the cardiac pulse compensation unit 112 includes a compliance unit 127. In some cases, the compliance unit 127 includes a compliance chamber 129 in fluid communication with the shunt passageway 106. The compliance chamber 129 receives CSF to displace a piston 131 biased, for example, by a spring or other actuation mechanism 133. As such, the piston 131 moves away from the shunt passageway 106 when pressure suddenly increases and toward the shunt passageway 106 when pressure suddenly decreases. In other configurations, the compliance chamber 129, piston 131, and actuation mechanism 133 are omitted and the compliance unit 127 is formed by the use of relatively flexible tubing forming the shunt passageway 106 to thereby dampen sudden pressure changes before the pressure changes are sufficiently present at the drainage valve inlet 119 to initiate actuation. One advantage of a compliance chamber 129 and piston 131 with a spring 133 is that such a compliance unit can allow for more precise control of the overall compliance of the ventricular system.

To derive an expression for the compliance C of the compliance unit 127, let $k_c$ be the spring constant of the spring 133, let $A_c$ be the cross-sectional area of the compliance chamber 129 and let $x_c$ be the relative displacement from equilibrium of the piston 131. The compliance of the compliance unit 127 is then the ratio of its volume change to pressure change, which is given by:

$$C = (x_c A_c)/(k_c x_c / A_c) = A_c^2 / k_c; \quad \text{Eqn. (1)}.$$

The total compliance of the ventricular system then is bounded from below by the compliance of the compliance unit 127. That is, the total compliance must be greater than or equal to the compliance of the compliance unit 127 because the native ventricular system will itself have a non-zero compliance.

In some situations, it may also be advantageous to increase the compliance of the intermediate passageway 122, so as to allow a time delay between closure of the forward valve 120 and actuation of the return valve 126. Such a situation may arise due to the flow characteristics of CSF in the shunt tubing. For instance, it may be preferable to wait for the forward valve 120 to close completely before opening valve 126, so that flow in the proximal passageway 102 is unidirectional at all times. In this case, one may insert a compliance unit 127 into the intermediate passageway 122.

Still referring to FIGS. 3 and 4, in some configurations the gravitational force compensation unit 114 compensates for gravitational effects on CSF pressure using a gravity compensation valve 128 (see FIG. 4) that automatically varies its actuation pressure differential threshold based on its orientation relative to gravitational forces (i.e., based on the orientation of the subject 10). To facilitate adjustability of its actuation pressure differential threshold, the gravity compensation valve 128 includes a passageway 130 in which a valve plug 132 (e.g., a valve ball or another type of plug that has an appropriate shape) seals against a seating surface 134 to prevent CSF flow through the passageway 130. The passageway 130 has a generally serpentine shape, and the valve plug 132 is disposed in the passageway 130 to actuate toward the inlet 135 of the valve 128 instead of the outlet 137 (i.e., the valve plug 132 is actuated upward when the subject stands upright). As such, when the valve 128 is oriented as shown in FIG. 4, CSF must overcome both the weight of the valve plug 132 and an elastic "pressure" $p_e$ applied by an elastic element 136 (e.g., a spring or the like) to open the outlet valve 128. In the case of a spring, the elastic pressure $p_e$ is as follows:

$$p_e = kx/A; \quad \text{Eqn (2)};$$

where k is the spring constant of the spring 136, x is the spring's deflection from an uncompressed state, and A is the cross-sectional area of the piston chamber 138.

Referring to FIGS. 1, 3, and 4, the weight of the valve plug 132 is preferably selected to counterbalance the gravitational siphoning effect on CSF pressure when the subject 10 stands upright. In this case, the optimal mass $M_P$ of the valve plug 132 is as follows:

$$M_P = M_{CSF} + \rho_{CSF} L A_T; \quad \text{Eqn. (3)}$$

where $M_{CSF}$ is the mass of the volume of CSF displaced by the valve plug 132, $\rho_{CSF}$ is the mass density of CSF, L is the elevation difference between the entry point of the shunt 102 to the ventricular system 12 and the entry point of the shunt 102 to the peritoneal cavity 14, and $A_T$ is the cross-sectional area of the shunt passageway 106.

On the other hand, when the subject 10 lies in a supine orientation (i.e., horizontally), the valve plug 132 actuates horizontally. In this orientation, gravity does not exert a CSF drainage force nor does the weight of the valve plug 132 act to block CSF outflow. In fact, as long as equation (3) is satisfied and as long as the axis of motion of the valve plug 132 is oriented such that opening of the valve 128 corresponds to movement of the valve plug 132 towards the vertex of the head, while closing of the valve 128 corresponds to movement of the valve plug 132 towards the chest, then the weight of the valve plug 132 should cancel the siphoning force due to CSF in the shunt tubing. To this point, equation (3) may be rewritten as follows:

$$(M_P - M_{CSF}) g \sin \theta = \rho_{CSF} L A_T g \sin \theta; \quad \text{Eqn. (4)}.$$

Here g is the gravitational constant and $\theta$ is the angle at which the valve plug 132 moves relative to a horizontal plane (i.e., the orientation of the subject 10 relative to the horizontal plane, so that $\theta = 0$ means that the subject is horizontal and $\theta = 90$ degrees means that the subject is upright. One then recognizes the left-hand side of equation (4) to be that part of the force acting on the valve plug 132 to close the valve, due to the weight of the valve plug, while the right hand side is the force acting to open the valve due to the siphoning effect. When the mass $M_P$ of the valve plug 132 is chosen as in equation (3), these two forces exactly cancel, regardless of the subjection's orientation.

When the siphoning force is exactly balanced by the mass of the valve plug 132, then the force acting to keep the gravity compensation valve 128 closed is the elastic spring 136. In this case, if $p_c$ is the pressure in the peritoneal cavity 14, then under steady-state conditions the average CSF pressure $p_i$ in the intermediate passageway 122 is as follows:

$$p_i = p_c + P_e; \quad \text{Eqn. (5)}.$$

As such, at steady-state conditions the average CSF pressure $p_i$ in the intermediate passageway 122 is constant and independent of the subject's orientation.

The steady-state average CSF pressure $p_i$ described above in turn affects the subject's steady-state average ICP. The value of the ICP, averaged over time, must fall within a certain range. The ICP, averaged over time, must be equal to or smaller than $p_{ICP, max}$, as follows:

$$p_{ICP, max} = p_i + \Delta_d \quad \text{Eqn. (6)}.$$

If the average ICP exceeds this threshold, the drainage valve 120 opens to permit CSF flow from the ventricular system 12 until the threshold is no longer exceeded. Conversely, the minimum average ICP $p_{ICP, min}$ is as follows:

$$p_{ICP, min} = p_i - \Delta_r \quad \text{Eqn. (7)}.$$

If the average ICP falls below this threshold, the return valve 126 opens to permit CSF to flow from the intermediate passageway 122 and return from the ventricular system 12 until the average ICP is no longer below this threshold.

From the above, it should be apparent that the maximum average ICP and the minimum average ICP depend on characteristics of the valves 120, 126, and 128 instead of gravity, cardiac pulse characteristics, or the like. As such, a subject's average ICP may be maintained in an appropriate range simply by designing and/or selecting appropriate valves.

It should also be noted that the above equations are valid if the shunt passageway 106 first tracks upwardly before turning downwardly toward the peritoneal cavity 14 as shown in FIG. 1. It is preferable that the highest point of the shunt tubing should be just a bit higher than the highest point of the native ventricular system 12. Conversely, if the shunt passageway 106 does not track upwardly, the weight of the CSF in the ventricular system 12 also acts on the valve assembly 110 to drain it in a direct way, independently of the siphoning effect. In this case, the effect of gravity on CSF drainage pressure $p_g$ is as follows:

$$p_g = \rho_{CSF} g (L(V/A_T));\qquad\text{Eqn. (8);}$$

where $\rho_{CSF}$, g, L, and $A_T$ are as described above, and V is the volume of the ventricular system 12.

Figure 5:
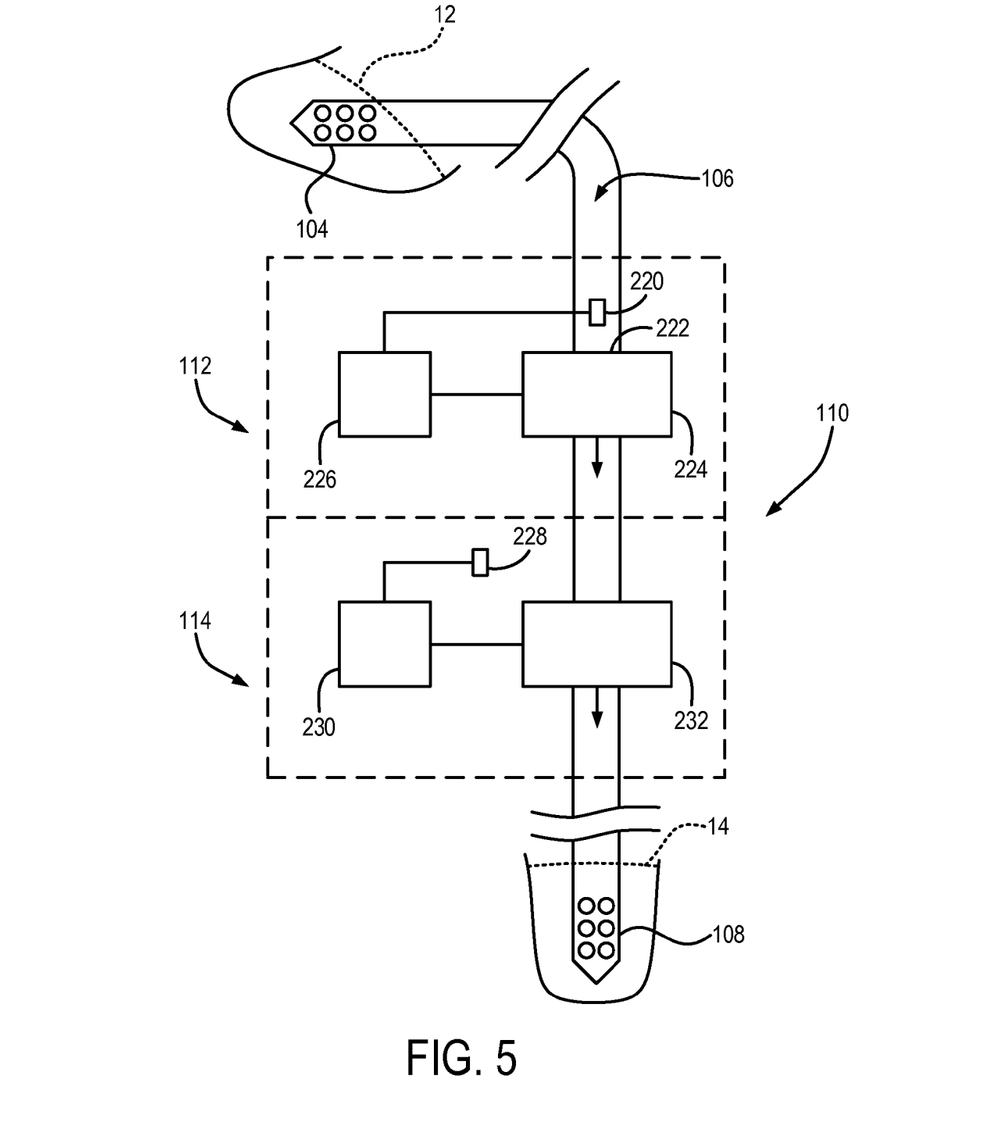
FIG. 5 is a schematic view of another configuration of the cardiac compensation unit and the gravitational force compensation unit of the valve assembly.

Referring now to FIG. 5 and as described briefly above, in some configurations the functionality of the cardiac pulse compensation unit 112 may be achieved using electrical/electronic mechanisms. In these configurations, the cardiac pulse compensation unit 112 may include one or more pressure sensors 220 that monitor CSF pressure at the inlet 222 of a drainage valve 224. When the inlet pressure exceeds a certain threshold due to excess CSF production, the pressure sensor 220 sends a signal to a controller 226, and the controller 226 then actuates the drainage valve 224. This action permits CSF flow from the ventricular system 12 and into the valve assembly 110. On the other hand, if the inlet pressure falls below a certain pressure threshold due to CSF over-drainage, the pressure sensor 220 also sends a signal to the controller 226 to actuate the drainage valve 224. This action permits CSF to flow from the valve assembly 110 and return to the ventricular system 12.

Similarly, in some configurations the functionality of the gravitational force compensation unit 114 may be achieved using electrical/electronic mechanisms. In these configurations, the gravitational force compensation unit 114 may include one or more orientation sensors 228, such as accelerometers, that monitor the orientation of the subject 10. The orientation sensor 228 sends a signal based on the subject's orientation to a controller 230, and the controller 230 adjusts the actuating pressure of an outlet valve 232 to compensate for CSF weight or siphoning effects as described above.

Figure 6:
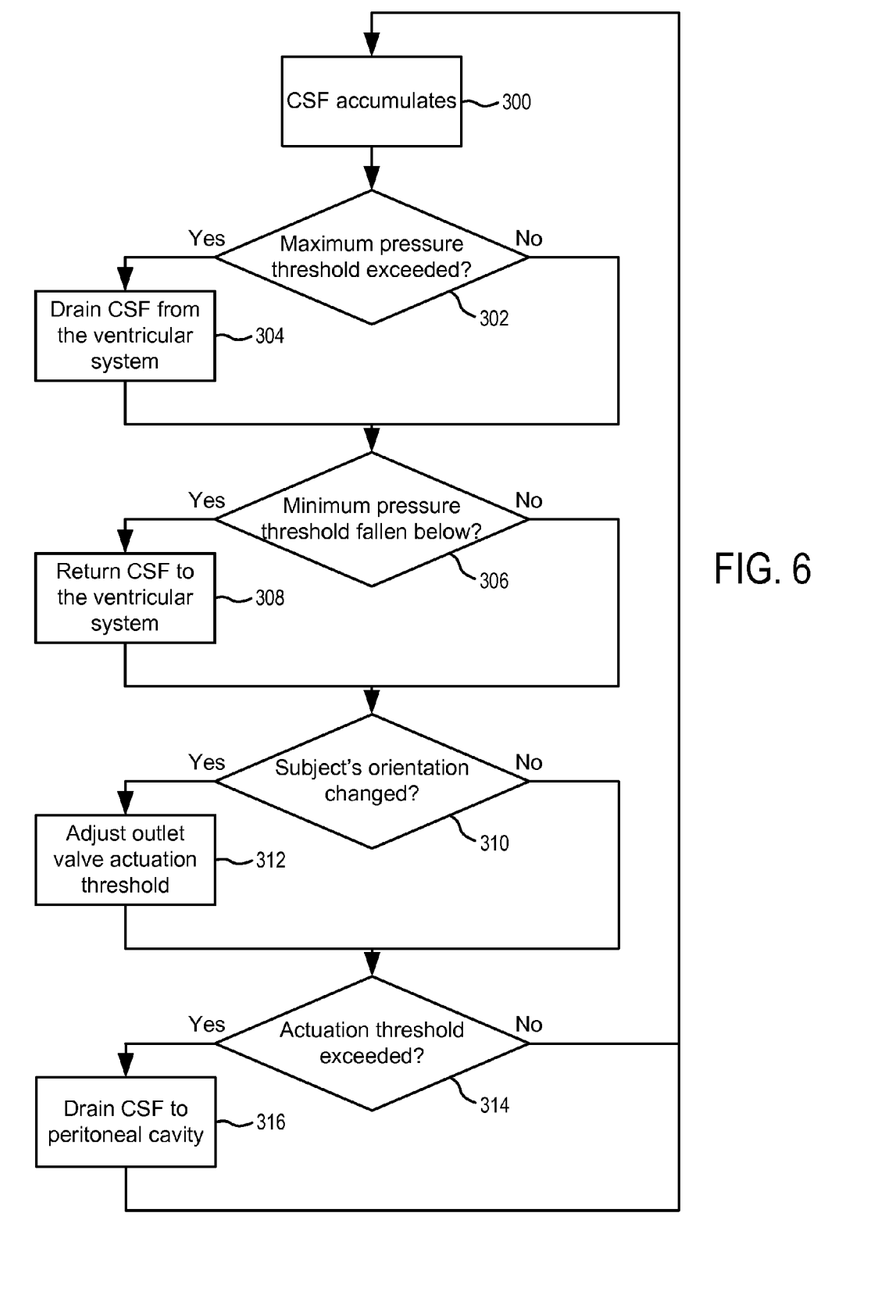
FIG. 6 is a flowchart illustrating steps performed by the system for controlling cerebrospinal fluid flow.

Referring now to FIG. 6, both configurations of the valve assembly 110 described above permit CSF to drain from the subject's ventricular system 12 under steady-state conditions as follows. First, CSF is produced and accumulates within the subject's ventricular system 12 at process block 300. As CSF accumulates, the cardiac pulse compensation unit 112 monitors the pressure to determine if the maximum ICP threshold has been exceeded at decision block 302. If the maximum ICP threshold has been exceeded, CSF is permitted to drain from the ventricular system 12 into the valve assembly 110 at process block 304. Thereafter, and also if the maximum ICP threshold has not been exceeded, the cardiac pulse compensation unit 112 determines if the CSF pressure has fallen below the minimum ICP threshold at decision block 306. If the CSF pressure has fallen below the minimum ICP threshold, CSF is permitted to return from the valve assembly 110 to the ventricular system 12 at process block 308. Thereafter, and also if the CSF pressure has not fallen below the minimum ICP threshold, the gravitational force compensation unit 114 determines if the subject's orientation has changed at decision block 310. If the subject's orientation has changed, the gravitational force compensation unit 114 adjusts the actuation threshold of its outlet valve at process block 312. Thereafter, and also if the subject's orientation has not changed, the gravitational force compensation unit 114 determines if the actuation threshold of its outlet valve has been exceeded at decision block 314. If the actuation threshold has been exceeded, CSF is permitted to drain from the valve assembly 110 toward the peritoneal cavity 14 at process block 316. Thereafter, and also if the actuation threshold has not been exceeded, the process returns to process block 300 and repeats indefinitely.

It should be apparent that the present invention provides systems and methods that compensate for multiple factors that can affect the subject's ICP and could otherwise lead to CSF over-drainage. The systems and methods compensate for these factors in a manner that inhibits the average ICP from deviating from a predetermined range. In particular, the shunt system drains excess CSF and relieves the increased ICP associated with hydrocephalus and inhibits CSF over-drainage and the decreased ICP that can lead to development of slit ventricle syndrome. The shunt system is also capable of altering net ventricular compliance so as to reduce symptoms of headache, in subjects in whom the native ventricular system is too stiff.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A system for controlling cerebrospinal fluid in a ventricular system of a subject, comprising:
    a shunt including:
        a drainage inlet configured to be disposed in the ventricular system of the subject to receive the cerebrospinal fluid;
        a drainage passageway in fluid communication with the drainage inlet to receive the cerebrospinal fluid;
        a drainage outlet in fluid communication with the drainage passageway to receive the cerebrospinal fluid, the drainage outlet being configured to be disposed in a region of the subject spaced apart from the ventricular system to drain the cerebrospinal fluid from the ventricular system;
    a cardiac pulse compensation unit connected to the shunt and including:
        a drainage valve configured to permit the cerebrospinal fluid to flow toward the drainage outlet when an input pressure of the cerebrospinal fluid at the drainage inlet exceeds a first pressure threshold;
        a return valve separate from and spaced apart from the drainage valve and configured to permit the cerebrospinal fluid to return to the ventricular system when the input pressure falls below a second pressure threshold; and
    a gravitational force compensation unit connected to the shunt and being configured to permit the cerebrospinal fluid to flow toward the drainage outlet when an input pressure of the cerebrospinal fluid at the gravitational force compensation unit exceeds a third pressure threshold, the gravitational force compensation unit varying the third pressure threshold such that a gravitational contribution to an intracranial pressure remains generally constant regardless of subject orientation.

2. The system of claim 1, wherein the cardiac pulse compensation unit further includes a return loop comprising:
an inlet branch in fluid communication with the drainage inlet and the gravitational force compensation unit, the inlet branch including the drainage valve; and
a return branch in fluid communication with the drainage inlet and the gravitational force compensation unit, the return branch including the return valve.

3. The system of claim 1, wherein the first pressure threshold is based only on characteristics of the drainage valve, the gravitational force compensation unit, and a pressure in the region of the subject spaced apart from the ventricular system, and the second pressure threshold is based only on characteristics of the return valve, the gravitational force compensation unit, and the pressure in the region of the subject spaced apart from the ventricular system.

4. The system of claim 3, wherein the gravitational force compensation unit includes an outlet valve having an elastic element that exerts an elastic pressure to resist flow of the cerebrospinal fluid through the outlet valve.

5. The system of claim 4, wherein the drainage valve is configured to permit the cerebrospinal fluid to flow therethrough when a drainage pressure differential threshold across the drainage valve is exceeded, and the first pressure threshold equals the elastic pressure plus the drainage pressure differential threshold and plus the pressure in the region of the subject spaced apart from the ventricular system.

6. The system of claim 4, wherein the return valve is configured to permit the cerebrospinal fluid to flow therethrough when a return pressure differential threshold across the return valve is exceeded, and the second pressure threshold equals the elastic pressure minus the return pressure differential threshold and plus the pressure in the region of the subject spaced apart from the ventricular system.

7. The system of claim 1, wherein the gravitational force compensation unit includes an outlet valve comprising:
a valve plug having a mass configured to resist the gravitational contribution such that the intracranial pressure remains generally constant regardless of subject orientation; and
an elastic element that exerts an elastic pressure against the valve plug to resist flow of the cerebrospinal fluid through the outlet valve.

8. A system for controlling cerebrospinal fluid in a ventricular system of a subject, comprising:
a shunt including:
a drainage inlet configured to be disposed in the ventricular system of the subject to receive the cerebrospinal fluid;
a drainage passageway in fluid communication with the drainage inlet to receive the cerebrospinal fluid;
a drainage outlet in fluid communication with the drainage passageway to receive the cerebrospinal fluid, the drainage outlet being configured to be disposed in a region of the subject spaced apart from the ventricular system to drain the cerebrospinal fluid from the ventricular system;
a passive valve assembly connected to the shunt and being configured to permit the cerebrospinal fluid to flow from the drainage inlet, through the drainage passageway, and toward the drainage outlet, the passive valve assembly operating without electrical sensors and controllers and including a pulse compensation element that decreases instantaneous cardiac pulse effects; and
wherein the valve assembly is configured to maintain an average intracranial pressure inclusively between a first pressure threshold and a second pressure threshold regardless of cardiac pulse effects and subject orientation.

9. The system of claim 8, wherein the valve assembly includes:
a drainage valve configured to permit the cerebrospinal fluid to flow from the drainage inlet toward the drainage outlet to maintain the average intracranial pressure at or below the first pressure threshold; and
a return valve configured to permit the cerebrospinal fluid to flow from the valve assembly toward the ventricular system to maintain the average intracranial pressure at or above the second pressure threshold.

10. The system of claim 9, wherein the drainage valve is configured to permit the cerebrospinal fluid to flow therethrough at an drainage flow rate, the return valve is configured to permit the cerebrospinal fluid to flow therethrough at a return flow rate, and the return flow rate is greater than the drainage flow rate.

11. The system of claim 9, wherein the valve assembly further includes an outlet valve configured to permit the cerebrospinal fluid to flow toward the drainage outlet when a pressure of the cerebrospinal fluid within the valve assembly exceeds a third pressure threshold, the outlet valve varying the third pressure threshold such that a gravitational contribution to the intracranial pressure remains generally constant regardless of subject orientation.

12. The system of claim 11, wherein the drainage passageway includes an intermediate passageway in fluid communication with an outlet of the drainage valve, an inlet of the return valve, and an inlet of the outlet valve.

13. A system for controlling cerebrospinal fluid in a ventricular system of a subject, comprising:
a shunt including:
a drainage inlet configured to be disposed in the ventricular system of the subject to receive the cerebrospinal fluid;
a drainage outlet in fluid communication with the drainage inlet to receive the cerebrospinal fluid, the drainage outlet being configured to be disposed in a region of the subject spaced apart from the ventricular system to drain the cerebrospinal fluid from the ventricular system;
a valve assembly connected to the shunt, including a drainage valve and a return valve separate from and spaced apart from the drainage valve, and being configured to:
1) permit the cerebrospinal fluid to flow from the drainage inlet and into the valve assembly when an input pressure of the cerebrospinal fluid exceeds a first pressure threshold;
2) permit the cerebrospinal fluid to flow from the valve assembly and return to the ventricular system when the input pressure falls below a second pressure threshold; and
3) permit the cerebrospinal fluid to flow from the valve assembly to the drainage outlet when an intermediate pressure of the cerebrospinal fluid within the valve assembly exceeds a third pressure threshold, the valve assembly varying the third pressure threshold such that a gravitational contribution to an intracranial pressure remains generally constant regardless of subject orientation.

14. The system of claim 13, wherein the valve assembly includes a drainage valve configured to permit the cerebrospinal fluid to flow from the drainage inlet and into the valve assembly when the input pressure of the cerebrospinal fluid exceeds the first pressure threshold.

15. The system of claim 13, wherein the valve assembly includes a return valve configured to permit the cerebrospinal fluid to flow from the valve assembly and return to the ventricular system when the input pressure falls below the second pressure threshold.

16. The system of claim 13, wherein the first pressure threshold and the second pressure threshold are based only on characteristics of the valve assembly and a pressure in the region of the subject spaced apart from the ventricular system.

17. A system for controlling cerebrospinal fluid in a ventricular system of a subject, comprising:
   a shunt including:
      a drainage inlet configured to be disposed in the ventricular system of the subject to receive the cerebrospinal fluid;
      a drainage passageway in fluid communication with the drainage inlet to receive the cerebrospinal fluid;
      a drainage outlet in fluid communication with the drainage passageway to receive the cerebrospinal fluid, the drainage outlet being configured to be disposed in a region of the subject spaced apart from the ventricular system to drain the cerebrospinal fluid from the ventricular system;
   a cardiac pulse compensation unit including a drainage valve and a return valve separate from the drainage valve, the cardiac compensation unit connected to the shunt and being configured to 1) permit the cerebrospinal fluid to flow from the drainage inlet toward the drainage outlet when an input pressure of the cerebrospinal fluid exceeds a first pressure threshold, and 2) permit the cerebrospinal fluid to return to the ventricular system when the input pressure falls below a second pressure threshold; and
   a gravitational force compensation unit connected to the shunt and being configured to permit the cerebrospinal fluid to flow from the drainage passageway to the drainage outlet when an input pressure of the cerebrospinal fluid at the gravitational force compensation unit exceeds a third pressure threshold, the gravitational force compensation unit varying the third pressure threshold such that a gravitational contribution to an intracranial pressure remains generally constant regardless of subject orientation.

18. The system of claim 17, wherein the gravitational force compensation unit includes an outlet valve having an elastic element that exerts an elastic pressure to resist flow of the cerebrospinal fluid through the outlet valve.

19. The system of claim 18, wherein the drainage valve is configured to permit the cerebrospinal fluid to flow therethrough when a drainage pressure differential threshold across the drainage valve is exceeded, and the first pressure threshold equals the elastic pressure plus the drainage pressure differential threshold and plus a pressure in the region of the subject spaced apart from the ventricular system.

20. The system of claim 18, wherein the return valve is configured to permit the cerebrospinal fluid to flow therethrough when a return pressure differential threshold across the return valve is exceeded, and the second pressure threshold equals the elastic pressure minus the return pressure differential threshold and plus a pressure in the region of the subject spaced apart from the ventricular system.

21. The system of claim 17, wherein the third pressure threshold is a pressure differential threshold.

22. The system of claim 17, wherein the cardiac pulse compensation unit includes a compliance unit configured to dampen sudden pressure changes of the cerebrospinal fluid.

* * * * *

UNITED STATES PATENT AND TRADEMARK OFFICE
CERTIFICATE OF CORRECTION

PATENT NO. : 8,876,744 B2
APPLICATION NO. : 13/040942
DATED : November 4, 2014
INVENTOR(S) : David Ambrose Hsu et al.

It is certified that error appears in the above-identified patent and that said Letters Patent is hereby corrected as shown below:

In the Specification

Column 6, line 26 - "$L_r$" should be --$\Delta_r$--

Column 8, line 41 - "$p_i = p_c + P_e$" should be --$P_i = p_c + p_e$--

Signed and Sealed this
Seventeenth Day of February, 2015

Michelle K. Lee
*Deputy Director of the United States Patent and Trademark Office*